United States Patent [19]

Bestwick et al.

[11] Patent Number: 5,421,121
[45] Date of Patent: Jun. 6, 1995

[54] FLORAL PRESERVATIVE METHOD AND COMPOSITION

[75] Inventors: Richard K. Bestwick, Portland; Vijaya K. Mokkapati, Beaverton, both of Oreg.

[73] Assignee: Epitope, Inc., Beaverton, Oreg.

[21] Appl. No.: 305,401

[22] Filed: Sep. 8, 1994

Related U.S. Application Data

[63] Continuation of Ser. No. 40,534, Mar. 30, 1993, abandoned.

[51] Int. Cl.$^6$ .......................... A01G 5/00; A47G 7/00; A01N 3/02; A61K 31/44
[52] U.S. Cl. ........................... 47/41.01; 47/58; 504/114; 504/115; 514/340
[58] Field of Search ............... 47/1.01, 41.01, 58.01, 47/58; 504/114, 115; 514/340

[56] References Cited

U.S. PATENT DOCUMENTS

| | | | |
|---|---|---|---|
| 3,865,569 | 2/1975 | Parups et al. | 504/114 |
| 3,874,871 | 4/1975 | Sy et al. | 504/114 |
| 3,907,539 | 9/1975 | Holdt et al. | 504/115 |
| 3,929,447 | 12/1975 | Beyer, Jr. et al. | 504/114 |
| 3,929,448 | 12/1975 | Brantley | 504/114 |
| 3,978,235 | 8/1976 | Schiro | 426/335 |
| 4,212,664 | 7/1980 | Takeuchi et al. | 71/94 |
| 4,322,237 | 3/1982 | Niggemann et al. | 504/115 |
| 4,966,908 | 10/1990 | Eckhardt et al. | 514/340 |
| 4,980,355 | 12/1990 | Zondler et al. | 514/256 |
| 5,080,707 | 1/1992 | Ide et al. | 504/115 |

FOREIGN PATENT DOCUMENTS 2189676 11/1987 United Kingdom .

OTHER PUBLICATIONS

Amrhein, N., and D. Wenker, "Novel inhibitors of ethylene production in higher plants," *Plant & Cell Physiol.* 20(8):1635–1642 (1979).

Kato, T., and S. Kataoka, "Plant-growth regulator containing hydrazine isonicotinate," Abstract No. 55257p from *Agro-chemicals* 76: 113 (1972).

*Primary Examiner*—David T. Fox
*Assistant Examiner*—Erich E. Veitenheimer
*Attorney, Agent, or Firm*—Peter J. Dehlinger; Vincent M. Powers

[57] ABSTRACT

Method for extending bloom life of a cut flower by bathing the flower in a solution which contains isoniazid. Also disclosed are compositions for use in the method.

5 Claims, 2 Drawing Sheets

FLORAL PRESERVATIVE METHOD AND COMPOSITION

This is a continuation of application Ser. No. 08/040,534, filed Mar. 30, 1993, now abandoned.

FIELD OF THE INVENTION

The present invention relates to floral preservative agents, and in particular, to use of isoniazid to extend the longevity of cut flowers.

REFERENCES

Baker, J. E., Wang, C. Y., Lieberman, M., and Hardenburg, R. (1977) Hort. Science 12: 38–39.

Beyer, E. M., Jr. (1976) Plant Physiol. 58: 268–271.

Fujino, D. W., Reid, M. S., and Yang, S. F. (1981) Acta Hortic. 113: 59–64.

Nowak, J., and Rudnicki, R. M. (1990) "Postharvest Handling and Storage of Cut Flowers, Florist Greens, and Potted Plants", A. A. Duncan, Ed., Timber Press, Portland, Oreg.

Reid, M. S., and Wu, M.-J. (1991) "Ethylene in Flower Development and Senescence" in "The Plant Hormone Ethylene", A. K. Mattoo and J. C. Suttle, Eds., CRC Press, Boca Raton, Fla., pp. 215–234.

Sisler, E. C., Reid, M. S., and Fujino, D. W., (1983) Acta Hortic. 141: 229–234.

Ward, T. M., Wright, M., Roberts, J. A., Self, R., and Osborne, D. J. (1978) "Analytical Procedures for the Assay and Identification of Ethylene", in *Isolation of Plant Growth Substances*, J. R. Hillman, Ed., Cambridge University Press, Cambridge.

BACKGROUND OF THE INVENTION

Although the useful lifetime of cut flowers can be extended by refrigeration and by use of certain chemical preservatives, the fact that many flower varieties are shipped as cut flowers over long distances has provided strong motivation to develop improved methods for extending flower bloom life. Placing cut flowers in water affords some measure of preservation by keeping the flowers hydrated, but chemical preservatives are often added to water solutions to extend bloom life further.

Among the chemical preservatives currently in use are carbohydrates such as sucrose, glucose, and fructose; acidifying agents for producing a solution pH of 3 to 7; and agents for preventing stem blockage (Nowak et al., 1990, page 44 et seq.). A number of preservative compositions which contain various mixtures of the above are commercially available, including Chrysal TM and Floralife TM, for example.

Other chemical preservatives currently in use include agents which appear to interfere with the action of ethylene, which plays an important role in senescence. Such preservatives include silver thiosulfate (STS), 2,5-norbornadiene, aminooxyacetic acid (AOA), and aminoethyoxyvinylglycine (AVG). Silver thiosulfate and 2,5-norbornadiene act by antagonistically blocking ethylene action. Aminooxyacetic acid and aminoethyoxyvinylglycine, on the other hand, act by inhibiting ethylene synthesis. Although these agents have been shown to be effective floral preservatives (Reid et al., 1991; Beyer, 1976; Sisler, 1983; Fujino et al., 1981; Baker et al., 1977) and are sometimes effective when used in combination with other chemical preservatives such as mentioned above, their toxicity and expense present significant drawbacks. Accordingly, new post-harvest floral preservatives that are non-toxic and environmentally safe have been sought.

Isoniazid has long been employed as a first-line drug in anti-tuberculosis therapy; however, use of isoniazid for increasing the longevity of cut flowers has not been known.

SUMMARY OF THE INVENTION

The present invention includes, in one aspect, a method of extending the longevity of a cut flower by bathing the cut end of the flower in an aqueous solution that contains isoniazid. In a preferred embodiment of the method, the concentration of isoniazid in the solution is from about 0.1 mM to about 10 mM, and is more preferably between about 1 mM and 10 mM.

In another aspect, the invention includes a composition for use in the above method. The composition includes isoniazid, a sugar nutrient, and an acidifying agent. Where the composition takes the form of an aqueous solution, the acidifying agent is preferably effective to afford a pH of between about 3 and about 7, more preferably between about 3 and about 6.

These and other objects and features of the invention will become more fully apparent when the following detailed description of the invention is read in conjunction with the accompanying drawings.

DETAILED DESCRIPTION OF THE INVENTION

A. Definitions

Figure 1:
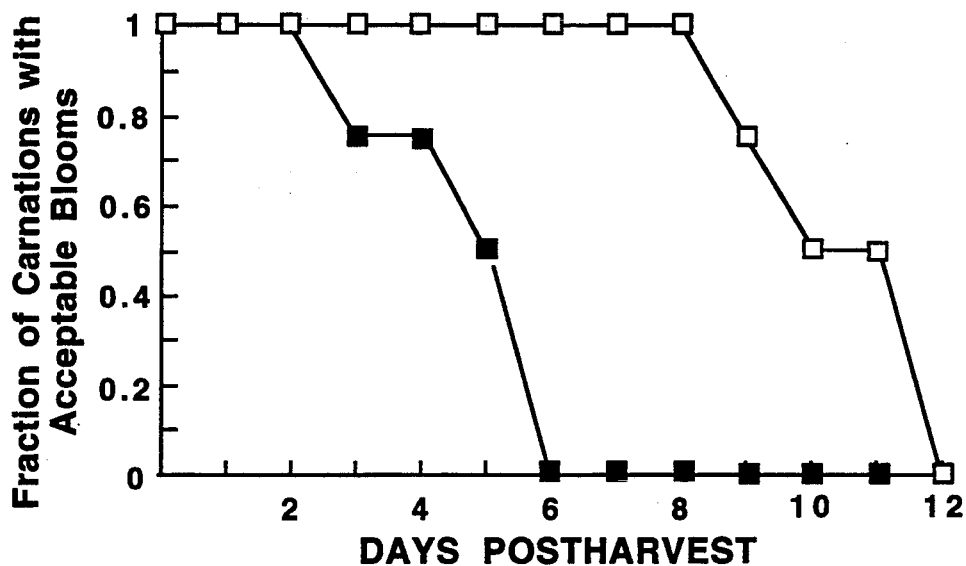
FIG. 1 shows a time course of acceptable bloom fraction in carnations following post-harvest storage in water (solid squares) and 5 mM isoniazid in water (open squares)

The terms defined in this section have the following meanings:

The "bloom life" of a flower is the time during which a flower shows an acceptable bloom. The time period, usually measured in days, begins at a selected starting time (e.g., the day on which the flower is cut at the stem from a living plant, or more typically, the day the flower is received pre-cut from a supplier), and ending on the last day the flower shows an acceptable bloom. An agent is said to extend the bloom life of a cut flower if bathing the flower in a solution that contains the agent results in a longer bloom life than would be obtained in the absence of the agent.

The definition of an acceptable bloom varies according to flower variety, but is generally defined as a bloom not showing signs of senescence. For carnations, signs of senescence include the appearance of brown petal tips or inrolling of petals. For roses, signs of senescence include the appearance of a bent neck, wilted petals, or blackening of the petal tips. When bloom life is reported collectively for a group of flowers, the reported value is the average of the bloom lives of the individual flowers in the group.

B. Use of Isoniazid as Floral Preservative

The present invention provides a method for extending the bloom life and general aesthetic appearance of a cut flower. In the method, the cut end of a flower is bathed or stored in a solution containing isoniazid at a concentration which is effective to extend the longevity of the flower. Isoniazid, also known as isonicotinic acid hydrazide, is commercially available as a free base and in various salt forms from a number of suppliers. Methods for preparing isoniazid are also well known.

The concentration of isoniazid which is effective for extending flower longevity varies according to flower variety. In general, the effective range is between about 0.1 and about 10 mM, typically between about 1 mM and about 10 mM, although concentrations beyond these ranges may also be useful. The flower can be placed in an isoniazid-containing solution immediately after harvest, or more typically, after receipt as a cut flower from a commercial supplier. The flower is usually stored at room temperature or below, for a period of several hours, e.g., about 3 hours, to a day or more, e.g., throughout the remaining bloom life of the flower.

The pH of the solution in which the cut flower is bathed can range from about 3 to about 9. In this regard, it is preferred that the isoniazid for use in the invention is obtained as the free base form, allowing the pH of the resultant solution to be adjusted using a suitable amount of acidifying agent, e.g., citric acid or an acidic form of inorganic phosphate $KH_2PO_4$ or phosphoric acid. Studies carried out in support of the invention indicate that longer bloom extension is achieved when the pH of the solution is acidic, i.e. between about 3 and about 7, and preferably between about 3 and about 6.

Conditions which are particularly effective for extending the bloom life of a selected variety of flowers can be developed on the basis of studies on relatively small groups of cut flowers (e.g., 200–500). Such studies are carried out using solutions containing various combinations of isoniazid and selected additive concentrations (e.g., carbohydrates, acidifying agents, stem blockage inhibitors, and the like) at one or more temperatures (e.g., at room temperature and at 4° C). Isoniazid concentrations tested in such a study can be 0.1, 0.5, 1, 3, and 10 mM, for example. Other additives in the study are likewise tested over a broad range of concentrations. Studies which illustrate the effectiveness of isoniazid for extending bloom life in cut flowers are described below.

The effectiveness of isoniazid as a preservative for carnations is illustrated by the data in FIG. 1. Eight greenhouse-grown White Sim carnations were cut after the blooms had reached the fully open stage of development (Stage II) and immediately placed in vials containing water (n=4) or 5 mM isoniazid in water (n=4). Individual carnations were then placed in quart mason jars with the lids removed and kept at room temperature. The bloom life of each flower was recorded as the last day the flower bloom was free from petal browning.

As can be seen from FIG. 1, one of four carnations which were stored in water (solid squares) showed petal browning by day 3 post-harvest, and only two of four (50%) still showed acceptable blooms on day 5. In contrast, all flowers stored in 5 mM isoniazid solution (open squares) showed acceptable blooms up to and including day 8 post-harvest; even after day 10, two of the four flowers still showed acceptable blooms. The results of this study show that the presence of isoniazid in the storage solution can delay the onset of senescence by 5 to 6 days in carnations.

Figure 2:
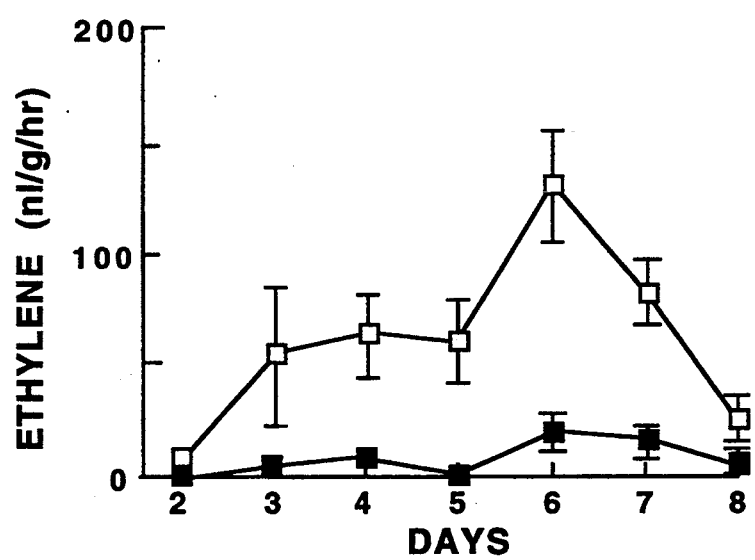
FIG. 2 shows ethylene production by the carnation samples from FIG. 1 stored in water (upper trace) and in 5 mM isoniazid in water (lower trace)

FIG. 2 shows ethylene production rates which were measured in the same carnations as above, by methods detailed in Example 1. In brief, ethylene production was assayed daily for each carnation by sealing each jar for 1 to 2 hours and then removing a 2 ml aliquot for gas chromatographic (GC) analysis. Flowers were weighed at the start of the experiment, and ethylene production was recorded in units of nl of ethylene/gram weight of carnation/hour.

With reference to FIG. 2, ethylene production in carnations stored in water (upper trace) rose from near zero on day 2 post-harvest to an average value of about 50 nl/g/hr on day 3. The rate remained steady for another two days, but on day 6 rose to about 120 nl/g/hr. Following day 6, ethylene production over the next two days fell to about 25 nl/g/hr on day 8. FIG. 1 shows that day 6 corresponded to the last day before bloom quality started to deteriorate in the carnation group stored in water.

The data for the carnations stored in 5 mM isoniazid (FIG. 2, lower trace), on the other hand, show that ethylene production in these carnations was substantially reduced, remaining at or below about 20 nl/g/hr throughout the monitoring period. Taken together with the data from FIG. 1, these data suggest that the bloom life extension brought on by isoniazid may arise from a reduction in the level of ethylene production.

Use of isoniazid in the context of preserving cut roses is illustrated in Example 2. Roses obtained via overnight air freight were removed from their packages, and nine roses each were placed in solutions of (i) a nutrient composition (EverGuard ™) and (ii) the same nutrient composition additionally containing 5 mM isoniazid (INH). EverGuard ™ is a sugar-containing nutrient solution which is commercially available from Agrimax, Inc. (St. Paul, Minn.). Similar nutrient supplements include Floralife ™ (available from Floralife Inc., Burr Ridge, Ill.), and Chrysal ™ (available from Pokon and Chrysal, Inc., Miami, Fla.). The bloom life of each flower was recorded as the last day the neck of the flower remained straight.

Figure 3:
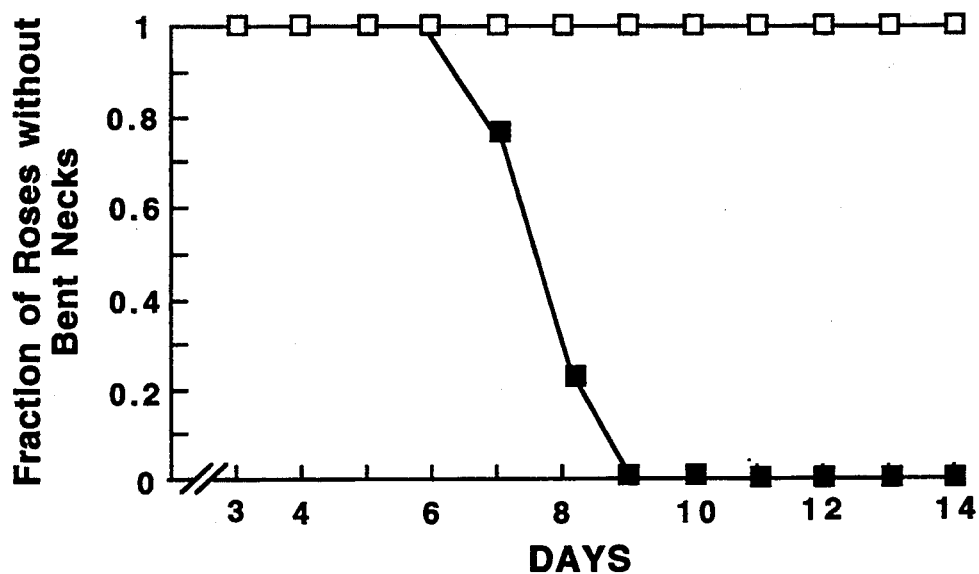
FIG. 3 illustrates the post-harvest onset of bent-neck in roses stored in a commercial nutrient solution (solid squares) and in the same nutrient solution additionally containing 5 mM isoniazid (open squares).

As can be seen from FIG. 3, the group of roses which were stored in the presence of nutrient without isoniazid began to exhibit bent necks on day 7 post-harvest (solid squares), with all having bent necks by day 9. In contrast, the roses stored in the solution which contained isoniazid in addition to nutrient (open squares) showed no evidence of bent necks even after 14 days, although some petal browning was observed (day 14). The above results illustrate the considerable improvement in the longevity of cut roses which can be achieved with isoniazid, i.e., as compared to sugar nutrient alone, isoniazid in combination with sugar nutrient can delay the onset of senescence in roses by 8 days.

While the above discussion illustrates use of isoniazid in extending bloom life for roses and carnations in particular, it is to be appreciated that isoniazid can be used advantageously with a wide variety of other flowers of interest to the cut flower industry. These include chrysanthemums, alstroemeria, gerbera, lilies, and "mini-carnations", for example.

C. Floral Preservative Composition

For distribution in a form which is readily transportable and ready for use, the isoniazid can be formulated as a dry powder to be taken up in aqueous solution. Such a composition may additionally include a carbohydrate such as typically used in the cut flower industry (e.g., sucrose, fructose, glucose, or the like), and an acidifying agent (e.g., citric acid or inorganic phosphate in an acidic form) which is effective to produce a pH of between about 3 and about 7, preferably between about 3 and about 6, when the composition is dissolved in an aqueous solution. As an example, such a composition in dry powder form can contain isoniazid, sucrose, and citric acid in proportions which, when the composition is dissolved in water, can provide a solution containing 5 mM isoniazid and 2 to 30% (w:v) sucrose, with a pH of 5 (maintained by citric acid). The composition may also contain a germicide (e.g., a quinoline compound) or the like, for deterring stem blockage. Preferably, the composition is formulated for the particular flower type of interest, according to the best conditions uncovered using studies such as above.

It will be seen from the foregoing how various objects and features of the invention are met. Isoniazid is effective at relatively low concentrations to extend the bloom life of cut flowers significantly. The compound is readily available and is generally safe for human handling, providing a significant improvement over many prior art preservatives.

The examples below illustrate but should not be taken to limit the scope of the invention.

EXAMPLE 1

Effect of Isoniazid on Ethylene Production in Carnations

Greenhouse-grown carnations (White Sim variety) were cut after the blooms had reached the fully open stage of development (Stage II). The step lengths were between 2 and 3 inches. The carnations were immediately placed in vials containing water or 5 mM isoniazid (free base form; Sigma Chemical Co., St. Louis, Miss.) in water. Individual carnations were then placed in quart mason jars with the lids removed and kept at room temperature for the remainder of the experiment.

The bloom life of each flower was recorded as the last day the flower bloom was free from petal wilting or browning. The results, reported as the fraction of flowers (n=4 for each of the two solutions tested) with acceptable bloom, are shown in FIG. 1.

Ethylene evolution in the above carnations was assayed daily by sealing each jar for 1 to 2 hours and then removing a 2 ml aliquot for gas chromatographic (GC) analysis. GC analysis was performed using a Hewlett Packard 5890 gas chromatograph equipped with a flame ionization detector and a 6 ft Porapak column as described by Ward et al. (1978). Data from the flame ionization detector were recorded using a Hewlett Packard Vectra computer running the current version of the Hewlett Packard "ChemStation" program, allowing measurements of ethylene as low as about 0.1 nL in a 2 ml sample (~0.05 ppm). Flowers were weighed at the start of the experiment, and ethylene production was recorded in units of nl of ethylene/hour/gram weight of the carnation (nl/g/hr).

FIG. 2 shows the time course of ethylene production recorded on day 2 through day 8 post-harvest, averaged for the flowers in water (n=4) and those in 5 mM isoniazid (n=4).

EXAMPLE 2

Effect of Isoniazid on Roses

Pre-cut roses were obtained from Agrimax, Inc. (St. Paul, Minn.) via overnight air freight. The roses were removed from their packages, and nine roses each were placed in solutions containing (i) EverGuard ® (Agrimax, Inc.) and (ii) EverGuard with 5 mM isoniazid.

Storage solutions were replenished as needed to offset volume loss, typically every 4 to 6 days. The bloom life of a given flower was recorded as the last day the neck of the flower was still straight. The results, reported as the fraction of flowers (n=9) without bent neck, are shown in FIG. 3.

Although the invention has been described with reference to various applications, methods, and compositions, it will be appreciated that various changes and modification may be made without departing from the invention.

It is claimed:

1. A method of extending bloom life of a cut flower of a rose or carnation, said method comprising
   bathing the stem of a cut flower in an aqueous solution containing isoniazid.
2. The method of claim 1, wherein the concentration of isoniazid in the solution is from about 1 mM to about 10 mM.
3. The method of claim 1, for use in extending bloom life of a carnation, wherein said bathing is effective to extend bloom life by at least 3 days over the bloom life achieved in the absence of isoniazid.
4. The method of claim 1, for use in extending bloom life of a rose, wherein said bathing is effective to extend bloom life by at least 3 days over the bloom life achieved in the absence of isoniazid.
5. The method of claim 1, wherein said solution additionally contains a carbohydrate selected from the group consisting of sucrose, fructose and glucose.

* * * * *